United States Patent
Milliman

(10) Patent No.: US 8,141,763 B2
(45) Date of Patent: Mar. 27, 2012

(54) ANVIL ASSEMBLY WITH IMPROVED CUT RING

(75) Inventor: Keith L. Milliman, Bethel, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 944 days.

(21) Appl. No.: 11/728,698

(22) Filed: Mar. 27, 2007

(65) Prior Publication Data

US 2007/0181632 A1    Aug. 9, 2007

Related U.S. Application Data

(63) Continuation of application No. 11/081,364, filed on Mar. 16, 2005, now Pat. No. 7,494,038.

(60) Provisional application No. 60/554,564, filed on Mar. 19, 2004.

(51) Int. Cl.
*A61B 17/115* (2006.01)

(52) U.S. Cl. .............. 227/179.1; 227/19; 227/180.1; 227/181.1

(58) Field of Classification Search ............ 227/19, 227/175.1, 176.1, 178.1, 179.1, 180.1, 181.1
See application file for complete search history.

(56) References Cited

U.S. PATENT DOCUMENTS

| | | | |
|---|---|---|---|
| 2,651,241 A | 9/1953 | Hornbostel | |
| 3,388,847 A | 6/1968 | Kasulln et al. | |
| 3,552,626 A | 1/1971 | Astafiev | |
| 3,638,652 A | 2/1972 | Kelley | |
| 4,198,982 A | 4/1980 | Fortner et al. | |
| 4,207,898 A | 6/1980 | Becht | |
| 4,289,133 A | 9/1981 | Rothfuss | |
| 4,304,236 A | 12/1981 | Conta et al. | |
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A * | 10/1984 | Kanshin et al. | 606/153 |
| 4,485,817 A | 12/1984 | Swiggett | |
| 4,488,523 A | 12/1984 | Shichman | |
| 4,505,272 A | 3/1985 | Utyamyshev et al. | |
| 4,505,414 A | 3/1985 | Filipi | |
| 4,550,870 A | 11/1985 | Krumme et al. | |
| 4,573,468 A | 3/1986 | Conta et al. | |

(Continued)

FOREIGN PATENT DOCUMENTS

CA        908529       8/1972

(Continued)

OTHER PUBLICATIONS

International Serarh Report for corresponding PCT/US05/08876, date of mailing Dec. 13, 2005.

*Primary Examiner* — Rinaldi Rada
*Assistant Examiner* — Nathaniel Chukwurah

(57) ABSTRACT

An anvil assembly for use with a surgical stapler is provided. The anvil assembly includes a cut ring assembly having a body and a cover. The cover has a first layer of material having a first hardness to allow penetration by a knife of a surgical stapler and at least one additional layer of material having a second hardness greater than the first hardness to minimize penetration of the cover by a knife of a surgical stapler.

46 Claims, 7 Drawing Sheets

U.S. PATENT DOCUMENTS

| | | |
|---|---|---|
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,754,909 A | 7/1988 | Barker et al. |
| 4,817,847 A | 4/1989 | Redtenbacher et al. |
| 4,873,977 A | 10/1989 | Avant et al. |
| 4,893,622 A | 1/1990 | Green et al. |
| 4,903,697 A * | 2/1990 | Resnick et al. ............ 227/178.1 |
| 4,907,591 A | 3/1990 | Vasconcellos et al. |
| 4,917,114 A | 4/1990 | Green et al. |
| 4,957,499 A | 9/1990 | Lipatov et al. |
| 4,982,639 A | 1/1991 | Kirkpatrick |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A * | 5/1994 | Grant et al. ................ 227/179.1 |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Bianco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,445,644 A | 8/1995 | Pietrafitta et al. |
| 5,447,514 A | 9/1995 | Gerry et al. |
| 5,454,825 A | 10/1995 | Van Leeuwen et al. |
| 5,470,006 A | 11/1995 | Rodak |
| 5,474,223 A | 12/1995 | Viola et al. |
| 5,497,934 A | 3/1996 | Brady et al. |
| 5,515,757 A | 5/1996 | O'Connor et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,632,433 A | 5/1997 | Grant et al. |
| 5,639,008 A | 6/1997 | Gallagher et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,758,814 A | 6/1998 | Gallagher et al. |
| 5,799,857 A | 9/1998 | Robertson et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,962,120 A * | 10/1999 | Keipert ...................... 428/317.9 |
| 5,993,468 A | 11/1999 | Rygaard |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balázs et al. |
| 6,264,086 B1 | 7/2001 | McGuckin, Jr. |
| 6,269,997 B1 | 8/2001 | Balázs et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,440,347 B1 | 8/2002 | Izawa et al. |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,623,227 B2 | 9/2003 | Scott et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,716,222 B2 | 4/2004 | McAlister et al. |
| 6,716,233 B1 | 4/2004 | Whitman |
| 6,742,692 B2 | 6/2004 | Hartwick |

| | | |
|---|---|---|
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,827,246 B2 | 12/2004 | Sullivan et al. |
| 6,840,423 B2 | 1/2005 | Adams et al. |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 2001/0000903 A1 | 5/2001 | Heck et al. |
| 2001/0010320 A1 | 8/2001 | Bolduc et al. |
| 2001/0054636 A1 | 12/2001 | Nicolo |
| 2002/0020732 A1 | 2/2002 | Adams et al. |
| 2002/0047036 A1 | 4/2002 | Sullivan et al. |
| 2002/0063143 A1 | 5/2002 | Adams et al. |
| 2002/0185516 A1 | 12/2002 | Heck et al. |
| 2002/0185517 A1 | 12/2002 | Vresh et al. |
| 2003/0019905 A1 | 1/2003 | Adams et al. |
| 2003/0047582 A1 | 3/2003 | Sonnenschein et al. |
| 2003/0057251 A1 | 3/2003 | Hartwick |
| 2003/0065342 A1 | 4/2003 | Nobis et al. |
| 2003/0073981 A1 | 4/2003 | Whitman et al. |
| 2003/0089757 A1 | 5/2003 | Whitman |
| 2003/0111507 A1 | 6/2003 | Nunez |
| 2003/0127491 A1 | 7/2003 | Adams et al. |
| 2003/0132267 A1 | 7/2003 | Adams et al. |
| 2003/0144675 A1 | 7/2003 | Nicolo |
| 2003/0178465 A1 | 9/2003 | Bilotti et al. |
| 2003/0183671 A1 | 10/2003 | Mooradian et al. |
| 2003/0192936 A1 | 10/2003 | Hartwick |
| 2003/0192937 A1 | 10/2003 | Sullivan et al. |
| 2003/0201301 A1 | 10/2003 | Bolduc et al. |
| 2003/0218047 A1 | 11/2003 | Sharma et al. |
| 2003/0222117 A1 | 12/2003 | Orban, III |
| 2004/0092960 A1 | 5/2004 | Abrams et al. |
| 2004/0092974 A1 | 5/2004 | Gannoe et al. |
| 2004/0118896 A1 | 6/2004 | Sharma et al. |
| 2004/0134964 A1 | 7/2004 | Adams et al. |
| 2004/0153124 A1 | 8/2004 | Whitman |
| 2004/0195289 A1* | 10/2004 | Aranyi ................ 227/180.1 |
| 2004/0232198 A1 | 11/2004 | Adams et al. |
| 2005/0051597 A1 | 3/2005 | Toledano |
| 2005/0067454 A1 | 3/2005 | Vresh et al. |
| 2005/0080439 A1 | 4/2005 | Carson et al. |
| 2005/0087580 A1 | 4/2005 | Orban, III |
| 2005/0107813 A1 | 5/2005 | Gilete Garcia |
| 2005/0116009 A1 | 6/2005 | Milliman |
| 2005/0125009 A1 | 6/2005 | Perry et al. |
| 2005/0143758 A1 | 6/2005 | Abbott et al. |
| 2005/0145674 A1 | 7/2005 | Sonnenschein et al. |
| 2005/0145675 A1 | 7/2005 | Hartwick et al. |
| 2005/0228446 A1 | 10/2005 | Mooradian et al. |

FOREIGN PATENT DOCUMENTS

| | | |
|---|---|---|
| DE | 1057729 | 5/1959 |
| DE | 3301713 | 11/1989 |
| EP | 0152382 | 8/1985 |
| EP | 0173451 | 3/1986 |
| EP | 0190022 | 8/1986 |
| EP | 282157 | 9/1988 |
| EP | 0503689 | 9/1992 |
| FR | 1461464 | 12/1966 |
| FR | 1588250 | 4/1970 |
| FR | 1136020 | 12/1979 |
| FR | 2443239 | 12/1979 |
| GB | 1185292 | 3/1970 |
| GB | 2016991 | 9/1979 |
| GB | 2070499 | 9/1981 |
| NL | 7711347 | 10/1977 |
| WO | 8706448 | 11/1987 |
| WO | 8900406 | 1/1989 |
| WO | 9006085 | 6/1990 |
| WO | WO 03/030745 | 4/2003 |

* cited by examiner

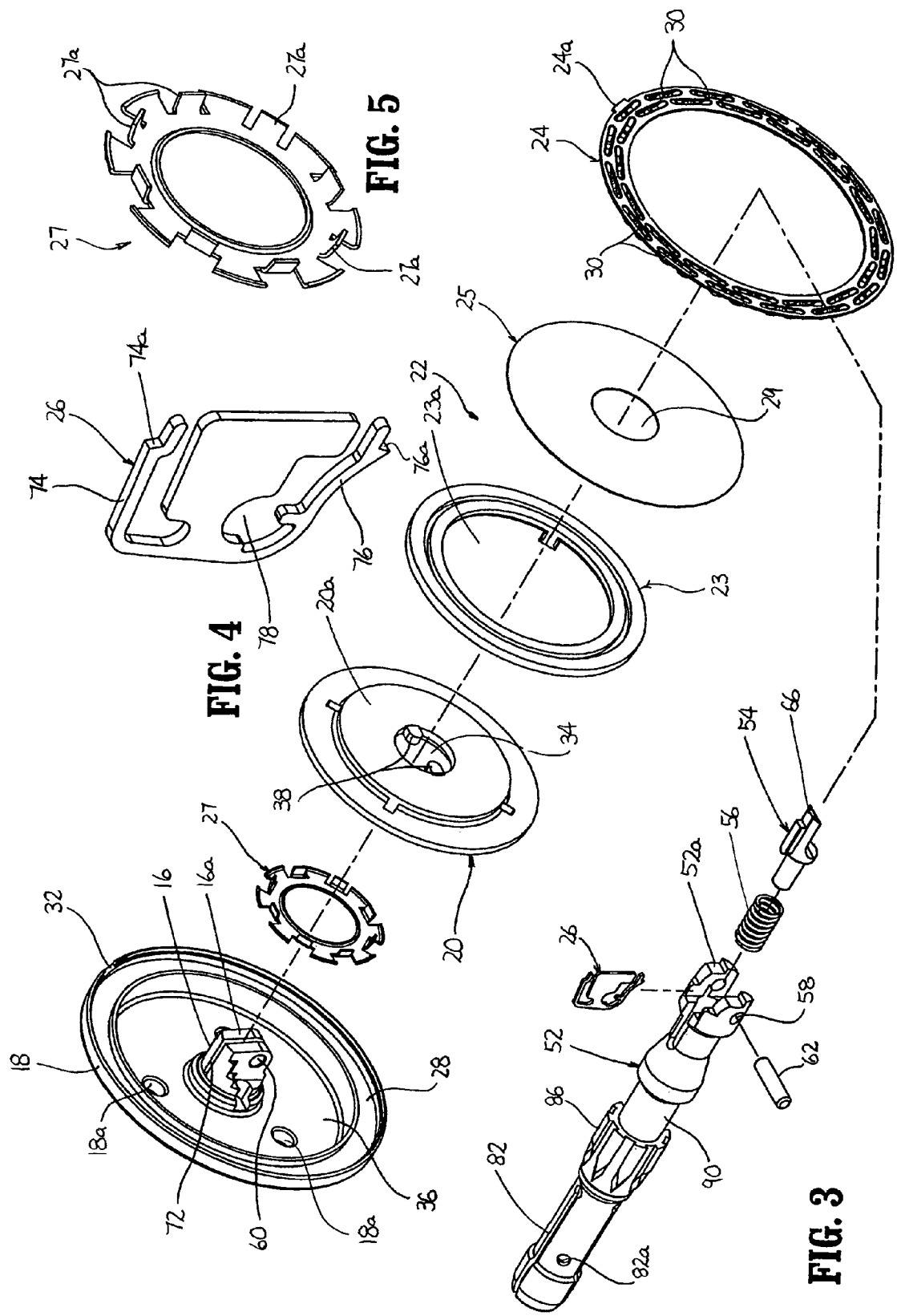

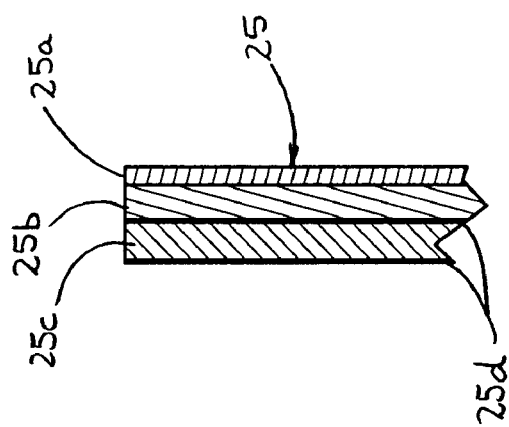
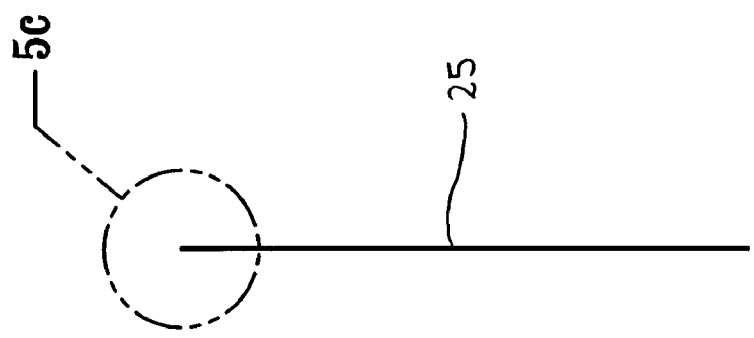
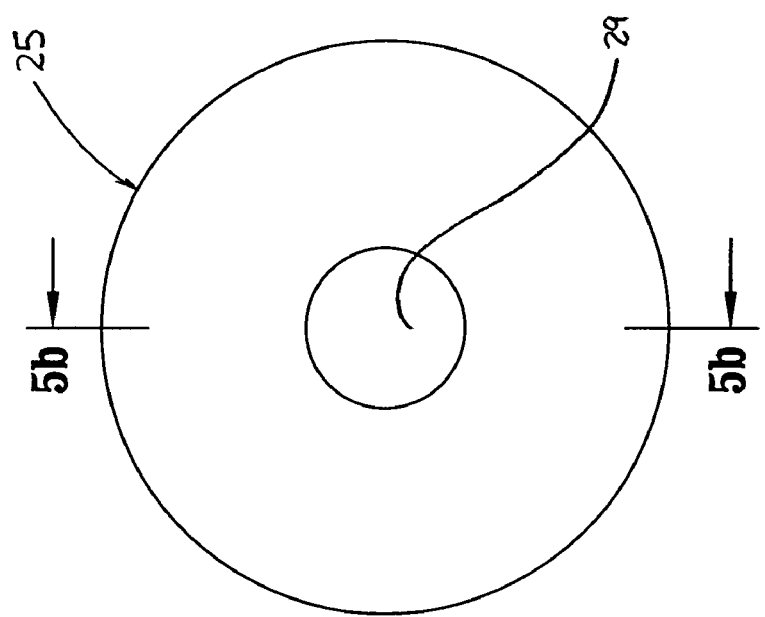

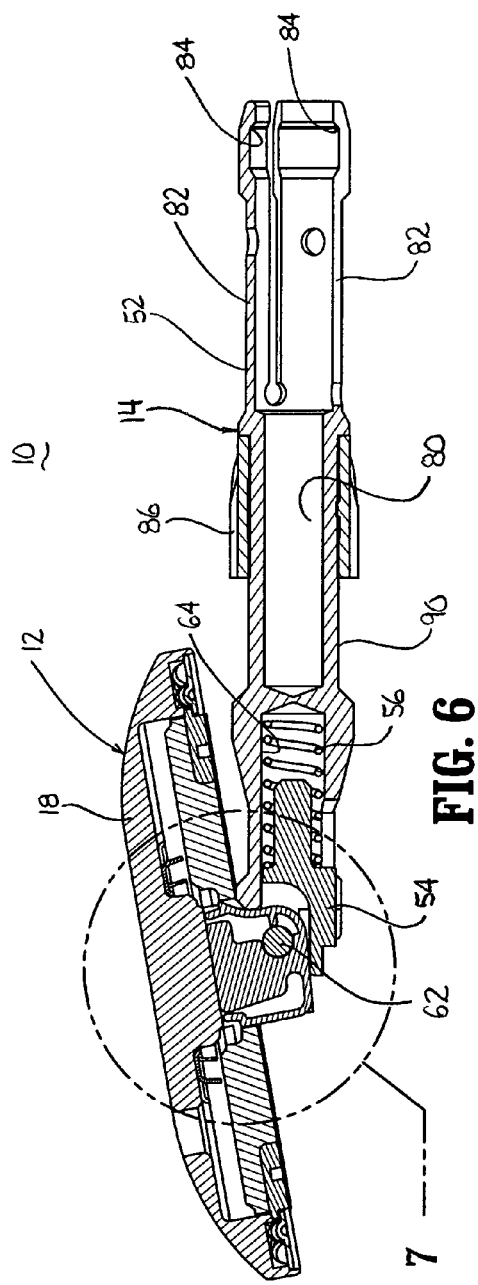
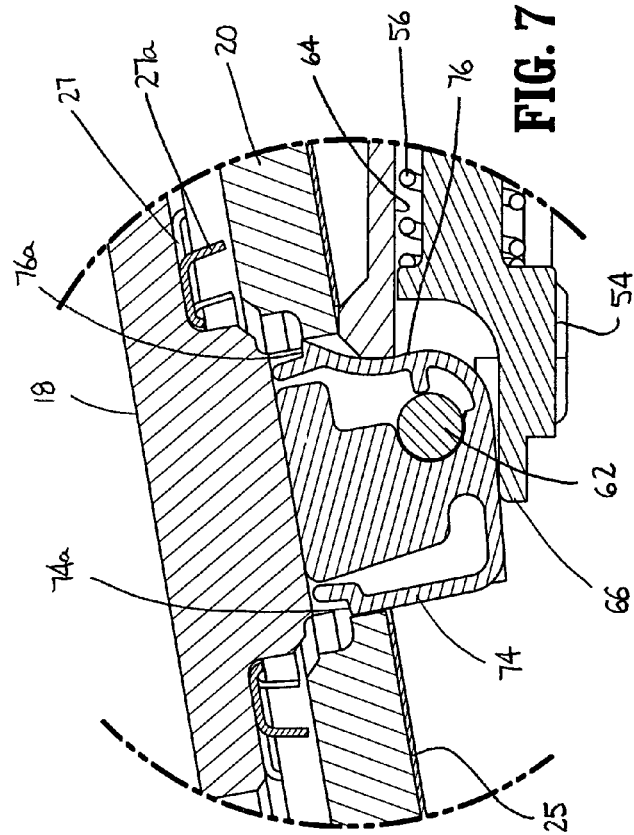
FIG. 6
FIG. 7

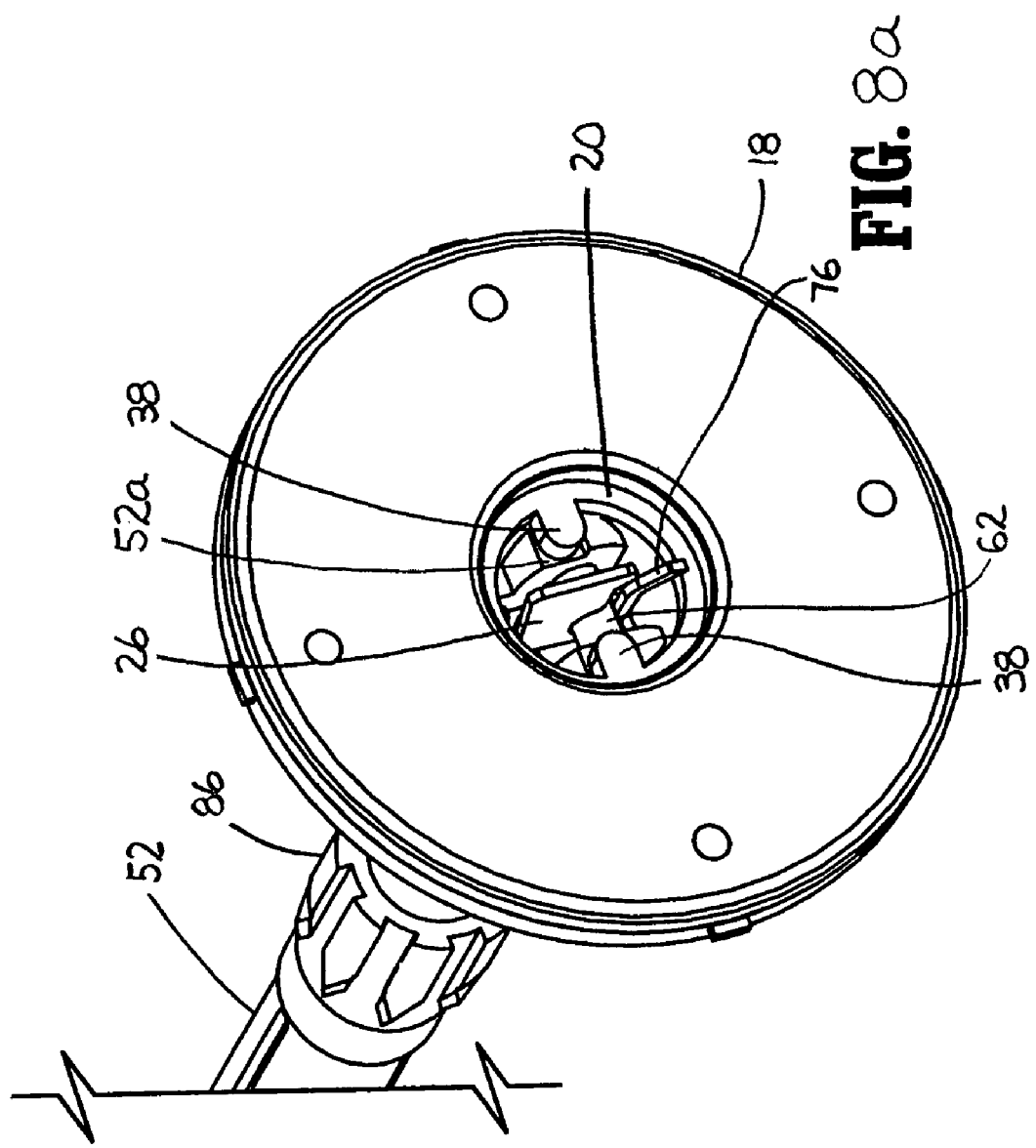

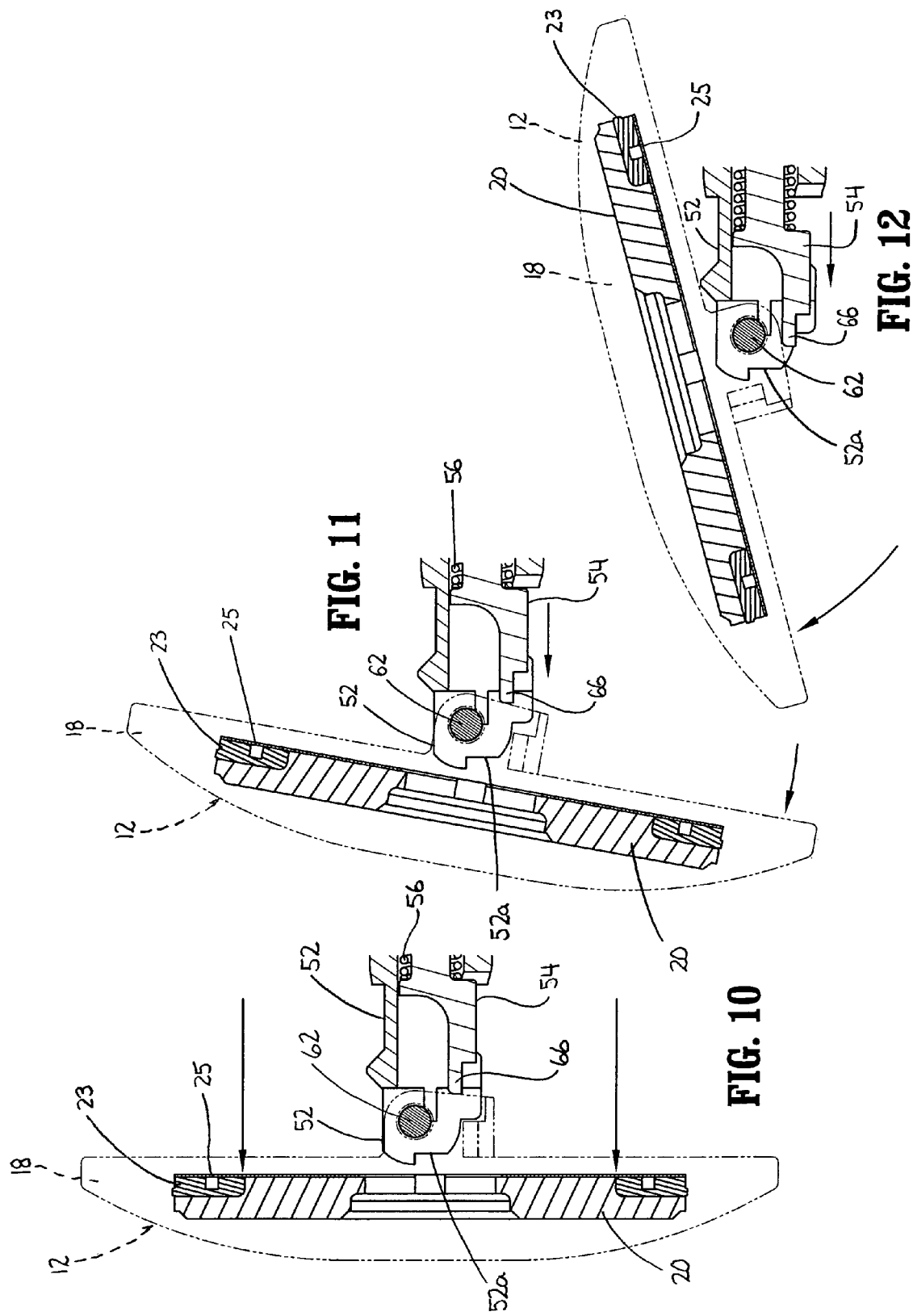

ANVIL ASSEMBLY WITH IMPROVED CUT RING

This application is a continuation of U.S. patent application Ser. No. 11/081,364 filed on Mar. 16, 2005 now U.S. Pat. No. 7,494,038 which claims priority to U.S. Provisional Application Ser. No. 60/554,564 filed on Mar. 19, 2004. The entire contents of each of these applications is incorporated herein by reference.

BACKGROUND

1. Technical Field

The present disclosure relates to an anvil assembly for use with a stapler. More specifically, the present disclosure relates to an anvil assembly having an improved cut ring particularly suited for use with a surgical stapler.

2. Background of Related Art

Anastomosis is the surgical joining of separate hollow tissue organ sections such that the hollow tissue organ sections communicate with each other. Typically, anastomosis follows surgery in which a diseased or defective section of hollow tissue is removed and the remaining end sections are to be joined. In a circular anastomosis procedure, the two ends of organ sections, e.g., the colon, are joined by means of a stapling instrument which drives a circular array of staples through the end sections of each organ section and simultaneously cores any overlapping tissue to free a tubular passage. Coring is effected by translation of an annular knife blade through the overlapping tissue.

Generally, a diseased or defective section of hollow tissue is removed using a linear stapling device which simultaneously cuts the hollow tissue and provides one or more linear rows of staples or fasteners on each side of the cut. The staples or fasteners seal the cut ends of the hollow tissue sections. This operation is performed on each end of the diseased or defective tissue such that each end of the diseased or defective hollow tissue and each end of the hollow tissue sections is sealed. Subsequently, a circular anastomosis stapling or fastener applying device is used to join the ends of the remaining hollow tissue sections and to core overlapping tissue.

The use of cut rings in anvil assemblies of circular anastomosis stapling or fastening devices are well known. Cut rings provide an abutment surface into which the annular knife blade of a circular anastomosis stapler abuts and/or penetrates during firing of the stapler to enhance cutting of tissue. Typically, cut rings are formed of a soft material, e.g., polyethylene, to allow some degree of knife penetration into the cut ring. During an anastomosis procedure, staples may inadvertently become positioned between the annular knife blade and the cut ring. In conventional staplers, because the cut ring is formed of a soft material, contact between the knife blade and a staple typically presses the staple into the cut ring and does not effectuate cutting of the staple.

Accordingly, a need exists for an improved surgical stapler which can not only effectively cut tissue but also effectively cut through existing staples in the tissue.

SUMMARY

In accordance with the present disclosure, an anvil assembly for use with a surgical stapling device is disclosed which includes an improved cut ring assembly. The cut ring assembly includes a body and a cover. The body may be formed from polyethylene, e.g., metallocene, although other materials of construction are contemplated. The cover may be formed from a plurality of layers of material. In one embodiment, the cover includes a first layer formed from polypropylene, a second layer formed from a relatively harder material such as a polyester, e.g., Mylar®, and a third layer formed of a harder material, e.g., polyester. It is also envisioned that the cover may include only two layers or four or more layers of material. In one embodiment, the first relatively soft layer is about 0.001 (0.0254 mm) inches in thickness and the second and third relatively hard layers are about 0.002 (0.0508 mm) inches in thickness. The layers may be fastened to each other and to the cut ring body using an adhesive. Alternately, other known fastening techniques may be used.

The first layer of the cut ring assembly cover is positioned to engage a knife blade of a surgical stapling device. The first layer is of a softness to allow penetration by the knife blade into the cut ring assembly to facilitate the severing of tissue by the knife blade. The second and third layers are of a hardness to substantially prevent or minimize penetration by the knife blade into the cut ring assembly to facilitate cutting of staples which may be inadvertently positioned between the knife blade and the cut ring within tissue to be joined by the surgical stapling device.

BRIEF DESCRIPTION OF THE DRAWINGS

Various embodiments of the presently disclosed anvil assembly are disclosed herein with reference to the drawings, wherein:

FIG. 3 is a side perspective exploded view from the proximal end of the anvil assembly shown in FIG. 1;

FIG. 4 is a side perspective view of the retaining clip of the anvil assembly shown in FIG. 1;

FIG. 5 is a side perspective view of the retainer member of the anvil assembly shown in FIG. 1;

FIG. 5a is a front-view of the cut ring assembly of the anvil assembly shown in FIG. 1;

FIG. 5b is a side cross-sectional view of the cut ring assembly taken along section lines 5b-5b of FIG. 5a;

FIG. 5c is an enlarged view of the indicated area of detail shown in FIG. 5b;

FIG. 6 is a side cross-sectional view of the anvil assembly shown in FIG. 1 with the head assembly in the tilted position;

FIG. 7 is an enlarged view of the indicated area of detail shown in FIG. 6;

FIG. 10 is a side cross-sectional view of the distal end of the anvil assembly shown in FIG. 1 with the head assembly in the non-tilted or operative position and the housing in phantom;

FIG. 11 is a side cross-sectional view of the distal end of the anvil assembly shown in FIG. 1 with the head assembly in a partially tilted position and the housing in phantom; and FIG. 12 is a side cross-sectional view of the distal end of the anvil assembly shown in FIG. 1 with the head assembly in the tilted position and the housing in phantom;

DETAILED DESCRIPTION OF EMBODIMENTS

Figure 2:
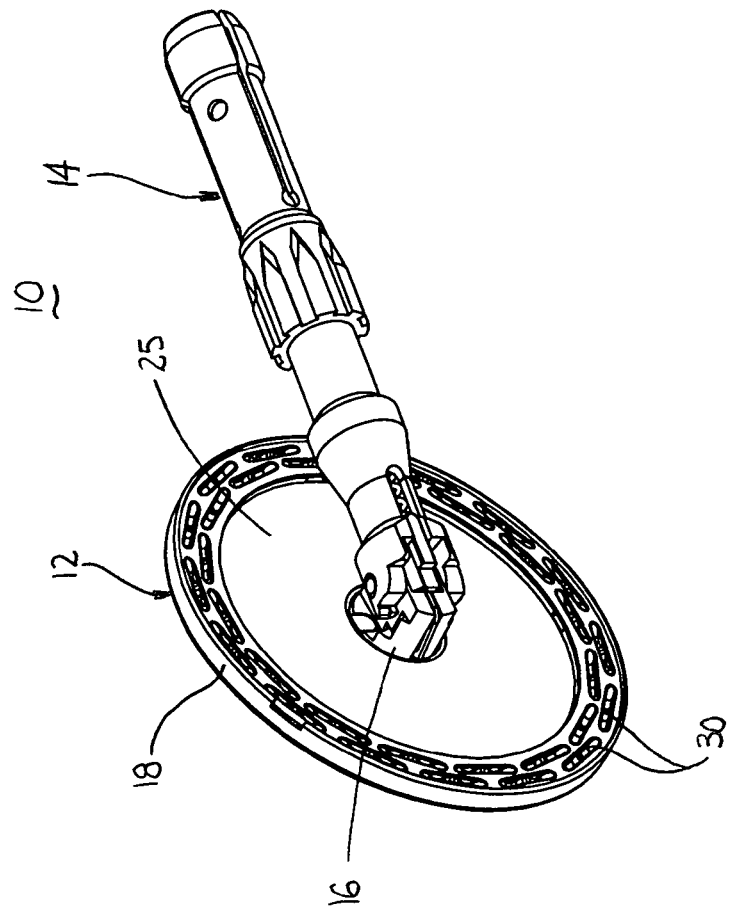
FIG. 2 is a side perspective view from the distal end of the anvil assembly shown in FIG. 1 with the head assembly in the tilted position.
Figure 1:
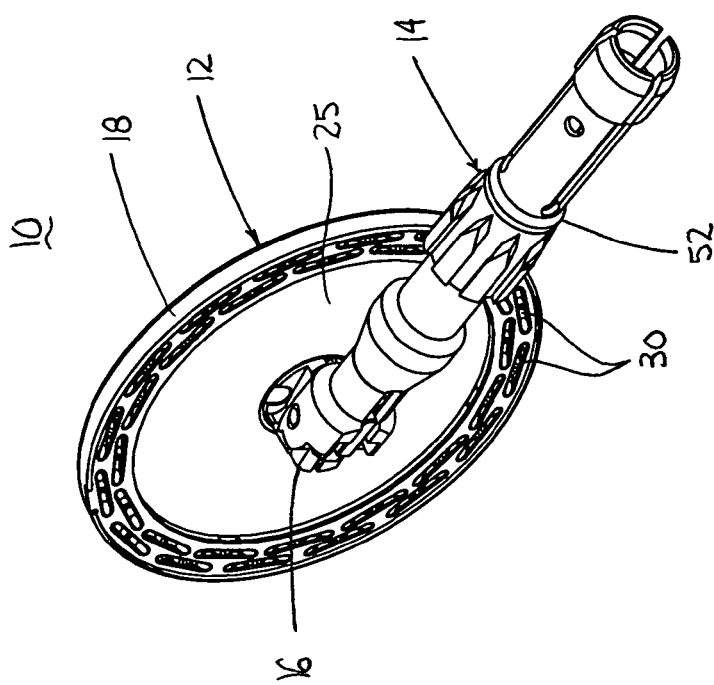
FIG. 1 is a side perspective view from the proximal end of one embodiment of the presently disclosed anvil assembly with the head assembly in the tilted position.

Embodiments of the presently disclosed anvil assembly 10 will now be described in detail with reference to the drawings in which like reference numerals designate identical or corresponding elements in each of the several views.

PCT application Serial No. PCT/US03/31638 ("PCT '638 application") and U.S. provisional application Ser. No. 60/512,482 ("'482 application") disclose surgical stapling devices suitable for use with the anvil assembly disclosed herein. These applications are incorporated herein by reference in their entirety.

FIGS. 1-12 illustrate an anvil assembly 10 which is suitable for use with a surgical stapling or fastener applying device for performing surgical procedures, e.g., circular anastomosis of hollow tissue organs, hemorrhoid removal and/or correction procedures, etc. Throughout this description the term "proximal" will refer to the portion of the device closest to the operator and the term "distal" will refer to the portion of the device furthest from the operator. Although this disclosure focuses primarily on an anvil assembly for deforming staples to join and/or seal tissue sections, it is contemplated that anvil assemblies for effecting closure of other known types of fasteners, e.g., two-part fasteners, energized sealing devices such as radio frequency sealing devices, etc., may also be used in association with the presently disclosed cut ring assembly. Further, although the presently disclosed cut ring assembly is illustrated in association with a tiltable anvil assembly, it is contemplated that the presently disclosed cut ring assembly may also be used in association with a non-tiltable anvil assembly.

As illustrated in FIGS. 1-4, anvil assembly 10 includes a head assembly 12 and a center rod assembly 14 which is pivotally secured to head assembly 12. Head assembly 12 includes a central post 16, a housing 18, a backup plate 20, a cut ring assembly 22, an anvil plate 24, a retaining clip 26, and a spacer member 27. In one embodiment, a top surface of housing 18 includes one or more pressure relief openings 18a (FIG. 3). Typically, post 16 is substantially centrally positioned through a bore (not shown) in head 18. Alternately, head 18 and post 16 may be integrally or monolithically formed. Anvil plate 24 is supported in an outer annular recess 28 of housing 18 and includes a plurality of staple deforming pockets 30 for receiving and deforming staples. In one embodiment, at least one tab 24a extends radially outwardly from anvil plate 24 and is received within a cutout 32 formed in an outer rim of housing 18. Tab 24a and cutout 32 function to align or properly locate and retain anvil plate 24 within annular recess 28 of housing 18.

Backup plate 20 includes a substantially centrally located opening 34 which is positioned about post 16 within an inner annular recess 36 of housing 18. Inner annular recess 36 is located between post 16 and outer annular recess 28. In one embodiment, backup plate 20 includes a raised center platform 20a although other configurations are envisioned. As shown, for instance, in FIG. 8, cut ring assembly 22 and backup plate 20 are slidably mounted about post 16. In one embodiment, backup plate 20 is formed of a hard material such as metal, e.g., sintered stainless steel, and includes a pair of inwardly extending fingers 38 which will be described in further detail below. Cut ring assembly 22 includes a body 23 and a cover 25. In one embodiment, body 23 is formed from a material softer than backup plate 20 such as polyethylene, e.g., metallocene, and includes an opening 23a having an inner configuration substantially the same as platform 20a to facilitate the positioning of cut ring assembly 22 about platform 20a. Although platform 20a is illustrated as having a circular shape, other configurations are envisioned, e.g., square, rectangular, triangular, etc. Cover 25 includes a substantially centrally located opening 29 for receiving post 16. Cut ring assembly 22 may be fixedly secured to backup plate 20 using, for example, an adhesive or by molding cut ring assembly 22 onto backup plate 20. Alternately other fastening techniques may be used to construct backup plate 20 and to secure backup plate 20 to cut ring assembly 22.

Referring to FIGS. 5A-5C, cut ring assembly 22 includes cover 25 which may be formed from a plurality of layers of material. In one embodiment, cover 25 includes a first layer 25a which is spaced from body 23 of cut ring assembly 22 by second and third layers 25b and 25c, respectively, and is formed from a relatively soft material, e.g., polypropylene, a second layer 25b is formed of a relatively hard material, e.g., a polyester such as Mylar® available from DuPont, and a third layer 25c formed of a relatively hard material, e.g., polyester such as Mylar®. It is contemplated that only one or more layers of relatively hard material may be provided to form cover 25 and that the relatively soft material may be eliminated. The layers 25a-c may be fastened together with an adhesive 25d or using other known fastening techniques. The first layer 25a is soft in relation to the second and third layers 25b and 25c to permit penetration by a knife blade of a surgical instrument into cut ring assembly 22 to enhance cutting of tissue. The second and third layers 25b and 25c have a hardness which is greater than the hardness of first layer 25a to provide a more rigid support for cutting staples which may inadvertently become positioned between a knife blade of a surgical stapling device and cut ring assembly 22. In a preferred embodiment, first layer 25a has a thickness in a range of between about 0.0005 inches and about 0.0015 inches and desirably having a thickness of about 0.001 inches (0.0254 mm) and second and third layers 25b and 25c have a thickness in a range of between about 0.0015 inches to about 0.0025 inches and desirably having a thickness of about 0.002 inches (0.0508 mm). In the alternative, other materials having different thicknesses may also be used to construct the different layers of cover 25 of cut ring assembly 22. Moreover, other material configurations may be used to form the relatively hard material layer(s), e.g., a braided, weaved, woven and non-woven materials.

Referring to FIGS. 3 and 5, spacer member 27 is annular and is positioned in inner annular recess 36 between backup plate 20 and a back wall of housing 18. In one embodiment, spacer member 27 is formed of a metal such as stainless steel or aluminum and includes a plurality of deformable tabs 27a which engage a rear surface of backup plate 20. Spacer member 27 prevents backup plate 20 and cut ring assembly 22 from moving or being pushed into inner annular recess 36 of housing 18 until a predetermined force sufficient to deform tabs 27a has been applied to the backup plate and cut ring assembly. In one embodiment, the predetermined force is close to but less than the force applied by an annular cutting blade of a stapling device to the cut ring assembly as the stapling device is fired. In one embodiment, the predetermined force is between about ten pounds (4.55 Kg) and about ninety pounds (40.9 Kg) and in another embodiment the predetermined force may be about fifty pounds. When the predetermined force is reached, e.g., during cutting of tissue, backup plate 20 and cut ring assembly 22 will move into inner annular recess 36 of housing 18 and compress spacer member 27. It is envisioned that other crushable, deformable, collapsible or movement restricting members may be used to retain the backup plate and cut ring assembly in a fixed position until a predetermined force has been applied to the backup plate and cut ring assembly.

Referring also to FIGS. 6 and 7, anvil center rod assembly 14 includes a center rod 52, a plunger 54 and plunger spring 56. A first end of center rod 52 has a transverse throughbore 58 (FIG. 3) which is offset from the central longitudinal axis of center rod 52. Post 16 of anvil head assembly 12 also includes a transverse throughbore 60 (FIG. 3). A pivot member 62 pivotably secures post 16 to center rod 52 via throughbores 58 and 60 such that anvil head assembly 12 is pivotably mounted to anvil center rod assembly 14.

Plunger 54 is slidably positioned in a bore 64 (FIG. 6) formed in the first end of center rod 52. Plunger 54 includes an engagement finger 66 shown in FIG. 7 which is offset from the pivot axis of anvil head assembly 12 and biased into engagement with the base 16a of post 16 (FIG. 3) by plunger spring 56 to urge anvil head assembly 12 from a non-tilted or operative position to a pivoted or tilted position on center rod 52. In a prefired position, fingers 38 formed on backup plate 20, shown in FIG. 3 as extending from backup plate 20 into central opening 34 of backup plate 20, engage a top surface 52a (FIG. 8a) of center rod 52 to prevent anvil head assembly 12 from pivoting about pivot member 62. When anvil assembly 10 is attached to a surgical stapling device and the device is fired such as disclosed in the PCT '638 and '482 applications, backup plate 20 and cut ring 22 are pushed into inner annular recess 36 of housing 18 about post 16 by an annular knife (not shown) to move fingers 38 out of engagement with top surface 52a of center rod 52 (FIG. 10) and permit plunger 54 to pivot anvil head assembly 12 about pivot member 62. Spacer member 27 prevents inadvertent or premature movement of the backup plate and cut ring assembly to prevent premature or inadvertent tilting of the head assembly 12.

Figure 9:
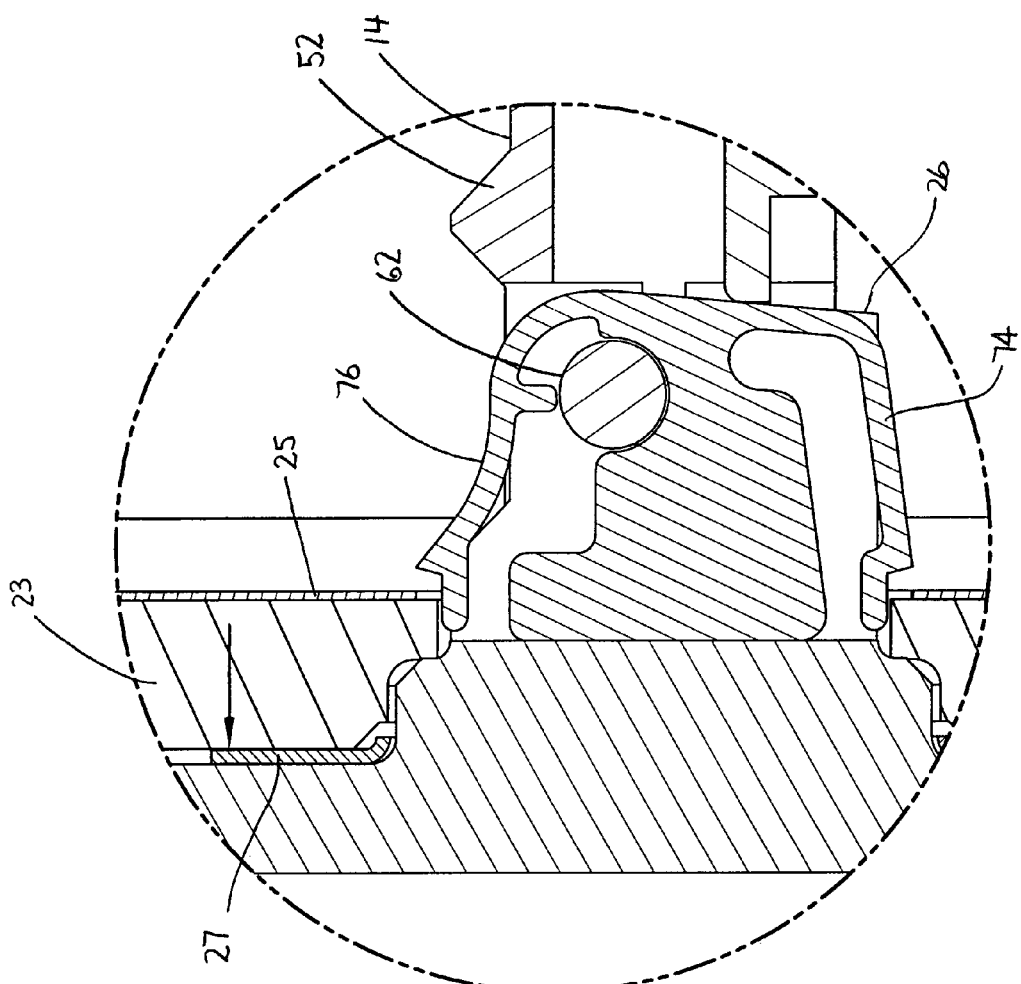
FIG. 9 is an enlarged view of the indicated area of detail shown in FIG. 8.
Figure 8:
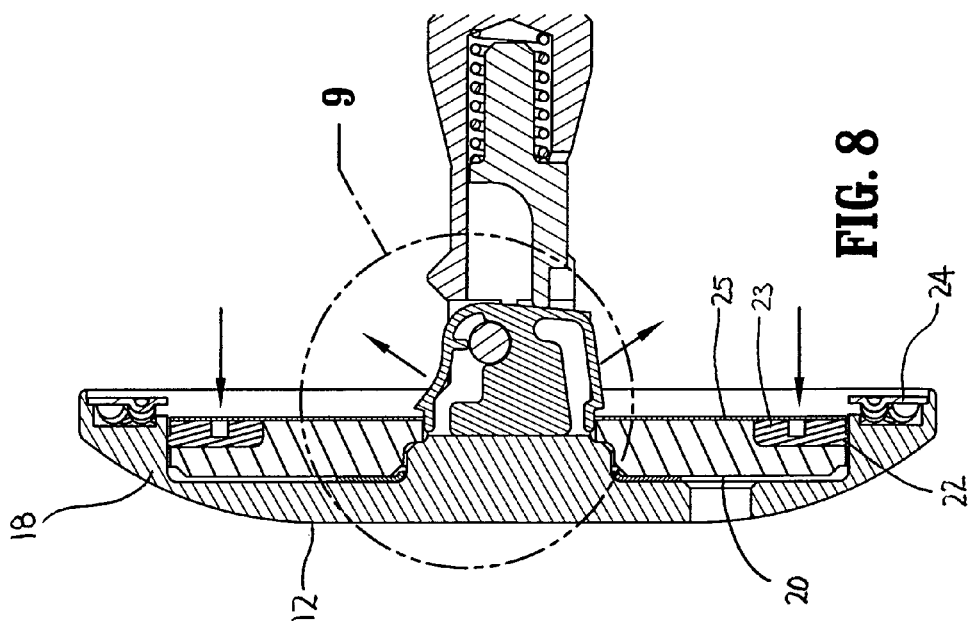
FIG. 8 is a side cross-sectional view of the distal end of the anvil assembly shown in FIG. 1 with the head assembly in the non-tilted or operative position.

Retaining clip 26 is positioned in a transverse slot 72 (FIG. 3) formed in post 16 and includes a pair of outwardly biased flexible arms 74 and 76 (FIG. 4). Arm 76 includes a recess 78 dimensioned to receive pivot pin 62. Each of arms 74 and 76 has a shoulder 74a and 76a, respectively. In one embodiment, retaining clip 26 is formed from a metal such as stainless steel, although other materials of construction are envisioned. Prior to movement of the backup plate and cut ring assembly into inner annular recess 36, backup plate 20 is positioned about post 16 to urge arms 74 and 76 of retaining clip 26 inwardly to a position within transverse slot 72 of post 16 (FIG. 7). After backup plate 20 has been pushed into inner annular recess 36 of housing 18 by a knife of a surgical stapler (not shown), flexible arms 74 and 76 spring radially outwardly to a position in which shoulders 74a and 76a are positioned in front of backup plate 20 and cut ring assembly 22 (FIG. 9). In this position, arms 74 and 76 prevent cut ring assembly 22 and backup plate 20 from sticking to the knife when anvil assembly 10 is moved away from the staple housing portion of the surgical stapling device.

Turning again to FIGS. 6 and 7, a second end of center rod 52 includes a bore 80 defined by a plurality of flexible arms 82. Flexible arms 82 each include an opening 82a dimensioned to receive a projection formed on or connected to a trocar (not shown) or to receive an adaptor connectable to an anvil retainer shaft (not shown) to releasably secure the trocar to center rod 52, or to releasably secure the adaptor to the anvil retainer shaft. The ends of each of flexible arms 82 include an internal shoulder 84 dimensioned to releasably engage the anvil retainer shaft or projection or adaptor connected to a surgical stapling device to secure the anvil assembly to the surgical stapling device. A plurality of splines 86 are formed about center rod 52. Splines 86 function to align anvil assembly 10 with a staple holding portion of a surgical stapling device. Center rod 52 also includes an annular recessed portion 90 to facilitate grasping of anvil assembly 10 by a surgeon with a grasper.

It will be understood that various modifications may be made to the embodiments disclosed herein. For example, the materials of construction disclosed herein may be substituted for with other materials of construction having the requisite strength requirements. Moreover, the anvil assembly may be of the removable type, as shown, or it may be permanently secured to a surgical stapler. Therefore, the above description should not be construed as limiting, but merely as exemplifications of embodiments.

What is claimed is:

1. An anvil assembly comprising:
 a head assembly including a housing supporting an anvil plate having a plurality of staple deforming pockets and a cut ring assembly supported within the housing adjacent the anvil plate, the cut ring assembly including a body and a cover fastened to a proximal surface of the body, the cover including a first layer formed of a first material having a hardness which allows penetration by a knife of a surgical stapler and at least one additional layer formed of a second harder material having a hardness to minimize penetration by a knife of a surgical stapler as the knife translates distally and engages the body and the cover.

2. An anvil assembly according to claim 1, wherein the cover is fastened to the body by an adhesive.

3. An anvil assembly according to claim 2, wherein the first layer is fastened to the at least one additional layer by an adhesive.

4. An anvil assembly according to claim 1, wherein the anvil plate and the cut ring assembly are annular and the cut ring assembly is positioned within a recess defined by the anvil plate.

5. An anvil assembly according to claim 4, wherein the head assembly further includes a central post extending from the housing, the anvil plate and the cut ring assembly being positioned about the central post.

6. An anvil assembly according to claim 5, further including an anvil center rod extending outwardly from the central post.

7. A cut ring assembly for use with an anvil assembly comprising:
 a body and a cover fastened to a proximal surface of the body, the cover including a first layer formed of a first material having a first hardness to allow penetration of the cover by a knife of a surgical stapler and at least one additional layer formed of a second material having a second hardness greater than the first hardness to minimize penetration of the cover by a knife of a surgical stapler as the knife translates distally along a knife path, wherein at least a portion of the body and at least a portion of the cover are positioned in the knife path.

8. A cut ring assembly according to claim 7, wherein the first layer of the cover is formed from polypropylene and the at least one second layer is formed from polyester.

9. A cut ring assembly according to claim 7, wherein the first layer is about 0.001 inches in thickness and the at least one second layer is about 0.002 inches in thickness.

10. A cut ring assembly according to claim 7, wherein the first and second layers are joined together using an adhesive.

11. A cut ring assembly according to claim 7, wherein the cover is fastened to the body using an adhesive.

12. A cut ring assembly according to claim 7, wherein the body is formed from polyethylene.

13. An anvil assembly comprising:
 a head assembly including a housing and an anvil plate, the anvil plate having a plurality of staple deforming pockets; and
 a cut ring assembly supported within the housing, the cut ring assembly including a body and a cover, the cover fastened to the body such that the body is positioned between a distal wall of the housing and the cover, wherein at least a portion of the cover is formed of a material that is harder than the body and minimizes penetration by a knife as the knife translates distally along a knife path and at least a portion of the body and at least a portion of the cover intersect the knife path.

14. An anvil assembly according to claim 13, wherein the cover is fastened to the body using an adhesive.

15. An anvil assembly according to claim 13, wherein the cover includes a first layer formed of a first material having a first hardness and at least one additional layer formed of a second material having a second hardness, the second material being harder than the first material.

16. An anvil assembly according to claim 15, wherein the first layer and the at least one additional layer are joined together using an adhesive.

17. An anvil assembly according to claim 15, wherein the first layer is formed from polypropylene and the at least one additional layer is formed from a polyester.

18. An anvil assembly according to claim 15, wherein the at least one additional layer includes a second layer and a third layer, the second and third layers being formed of the second harder material.

19. An anvil assembly according to claim 18, wherein the first layer is formed from polypropylene and the second and third layers are formed from polyester.

20. An anvil assembly according to claim 15, wherein the first layer is about 0.001 inches in thickness and at least one additional layer is about 0.002 inches in thickness.

21. An anvil assembly according to claim 13, wherein the anvil plate and the cut ring assembly are annular and the cut ring assembly is positioned within a recess defined by the anvil plate.

22. An anvil assembly according to claim 13, wherein the body is formed from polyethylene.

23. An anvil assembly according to claim 13, wherein the at least a portion of the cover is formed from polyester.

24. An anvil assembly for use with a surgical stapler having a proximal end closer to the user and a distal end further from the user, the anvil assembly comprising:
an anvil plate having a plurality of staple deforming pockets to deform staples fired by the surgical stapler;
an anvil rod having a longitudinal axis;
a backup plate;
a cover positioned proximally of the backup plate and extending radially through a knife path of the surgical stapler, the cover having a first layer having a first hardness and a second layer having a second hardness, the first layer positioned proximally of the second layer and the second hardness being greater than the first hardness; and
a knife translating along the knife path such that it engages the first and second layers of the cover as the knife travels distally along the knife path.

25. The anvil assembly of claim 24, further comprising a ring, the ring formed of material softer than a material of the backup plate.

26. The anvil assembly of claim 25, wherein the backup plate has a raised center platform.

27. The anvil assembly of claim 25, wherein the ring is fastened to the backup plate by adhesive.

28. The anvil assembly of claim 24, wherein the backup plate has a raised center platform.

29. The anvil assembly of claim 24, wherein the first layer of the cover is fastened to the second layer of the cover by adhesive.

30. The anvil assembly of claim 24, wherein the cover includes a third layer having a hardness greater than the first layer, the third layer positioned distally of the first layer.

31. The anvil assembly of claim 24, further comprising a spacer member positioned distally of the backup plate.

32. The anvil assembly of claim 24, wherein the spacer member includes a plurality of deformable tabs engaging the backup plate.

33. The anvil assembly of claim 24, wherein the backup plate moves distally upon advancement of the knife of the stapler.

34. The anvil assembly of claim 24, further comprising a housing having a recess to support the anvil plate.

35. The anvil assembly of claim 34, further comprising a ring positioned between the housing and cover.

36. An anvil assembly for use with a surgical stapler having a proximal end closer to the user and a distal end further from the user, a plurality of staples and a knife, the anvil assembly comprising:
a housing having a recess;
an annular anvil plate supported by the housing, the anvil plate having a plurality of staple deforming pockets to deform staples fired by the surgical stapler;
an annular backup plate having a proximally facing surface and positioned distally of the staple deforming pockets;
a cut ring positioned proximally of at least a portion of the proximally facing surface of the backup plate; and
a cover positioned proximally of the backup plate and configured to a receive a knife of the surgical stapler, the cover having a first layer having a first hardness and a second layer having a second hardness, the first layer positioned proximally of the second layer and the second hardness being greater than the first hardness to limit penetration of the knife as the knife translates distally and engages the first and second layers of the cover.

37. A cut ring assembly for use with an anvil assembly comprising:
a body and a cover fastened to the body, the cover including a first layer formed of a first material having a first hardness to allow penetration of the cover by a knife of a surgical stapler as the knife translates along a knife path and at least one additional layer formed of a second material having a second hardness greater than the first hardness to minimize penetration of the cover by a knife of a surgical stapler, wherein the at least one additional layer includes a second layer and a third layer, wherein at least a portion of the body and at least a portion of the cover intersect the knife path.

38. A cut ring assembly according to claim 37, wherein the first layer of the cover is formed from polypropylene and the at least one second layer is formed from polyester.

39. A cut ring assembly according to claim 38, wherein the first and second layers are joined together using an adhesive.

40. A cut ring assembly according to claim 39, wherein the cover is fastened to the body using an adhesive.

41. A cut ring assembly according to claim 38, wherein the body is formed from polyethylene.

42. An anvil assembly comprising:
a head assembly including a housing and an anvil plate, the anvil plate having a plurality of staple deforming pockets; and
a cut ring assembly supported within the housing, the cut ring assembly including a body and a cover, the cover fastened to the body such that the body is positioned between a distal wall of the housing and the cover, wherein at least a portion of the cover is formed of a material that is harder than the body;

wherein the cover includes a first layer formed of a first material having a first hardness and at least one additional layer formed of a second material having a second hardness, the second material being harder than the first material, the first layer and the at least one additional layer being joined together using an adhesive, wherein the first layer is formed from polypropylene and the at least one additional layer is formed from a polyester, and wherein the at least one additional layer includes a second layer and a third layer, the second and third layers being formed of the second harder material, such that distal translation of a knife engages the first and second layers of the cover.

43. An anvil assembly according to claim 42, wherein the cover is fastened to the body using an adhesive.

44. An anvil assembly according to claim 42, wherein the first layer is formed from polypropylene and the second and third layers are formed from polyester.

45. An anvil assembly according to claim 42, wherein the anvil plate and the cut ring assembly are annular and the cut ring assembly is positioned within a recess defined by the anvil plate.

46. An anvil assembly according to claim 42, wherein the body is formed from polyethylene.

* * * * *